United States Patent [19]
Willis et al.

[11] Patent Number: 6,066,333
[45] Date of Patent: May 23, 2000

[54] PHARMACEUTICAL CONTROL OF INFLAMMATION

[75] Inventors: Dean Willis, Atherstone; Adrian Richard Moore, Ilford; Derek Albert Willoughby, London, all of United Kingdom

[73] Assignee: William Harvey Research Limited, London, United Kingdom

[21] Appl. No.: 08/821,557

[22] Filed: Mar. 21, 1997

Related U.S. Application Data

[63] Continuation-in-part of application No. PCT/GB95/02249, Sep. 22, 1995.

[30] Foreign Application Priority Data

Sep. 22, 1994 [CA] Canada ................................. 2132690

[51] Int. Cl.[7] ........................................... A61K 9/20
[52] U.S. Cl. ..................... 424/464; 424/463; 424/489; 424/461
[58] Field of Search ................................ 424/464, 650, 424/639, 651; 514/185, 505, 410

[56] References Cited

U.S. PATENT DOCUMENTS

| | | | |
|---|---|---|---|
| 4,699,903 | 10/1987 | Rideout et al. | 514/185 |
| 5,010,073 | 4/1991 | Kappas et al. | 424/650 |
| 5,102,670 | 4/1992 | Abraham et al. | 514/185 |

FOREIGN PATENT DOCUMENTS

| | | |
|---|---|---|
| 2 263 111 | 7/1993 | United Kingdom . |
| WO 91/04667 | 4/1991 | WIPO . |
| WO 92/18112 | 10/1992 | WIPO . |
| WO 93/07114 | 4/1993 | WIPO . |
| WO 93/13055 | 7/1993 | WIPO . |
| WO 94/13252 | 6/1994 | WIPO . |

OTHER PUBLICATIONS

Cantoni, L. et al., "Interleukin–1 and tumor necrosis factor induce hepatic haem oxygenase: Feedback regulation by glucocorticoids," *Biochem. J.* 279:891–894 (1991).

*Primary Examiner*—Thurman K. Page
*Assistant Examiner*—William E. Benston, Jr.
*Attorney, Agent, or Firm*—Sterne, Kessler, Goldstein & Fox P.L.L.C.

[57] ABSTRACT

Control of inflammation is achieved by control of the level and/or activity of the enzyme heme-oxygenase (HO). A HO inducer is anti-inflammatory (FIG. 14) and used to treat inflammation, such as chronic inflammatory diseases. A HO inhibitor promotes inflammation and is used to treat immunosuppressed conditions. Alternative, or additional, control of heme-oxygenase activity is achieved by control of nitric oxide levels, elevated levels promoting inflammation.

9 Claims, 9 Drawing Sheets

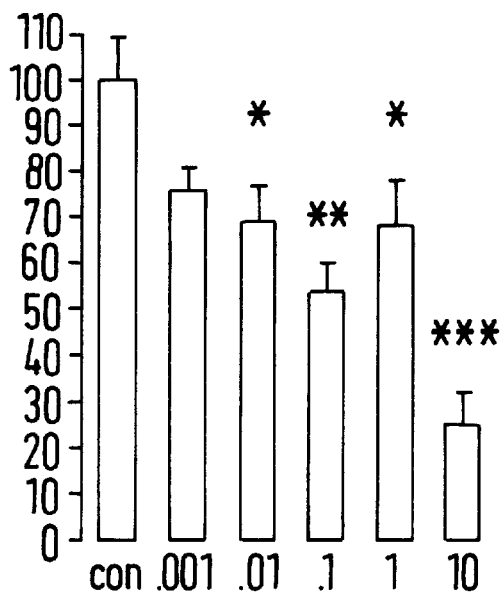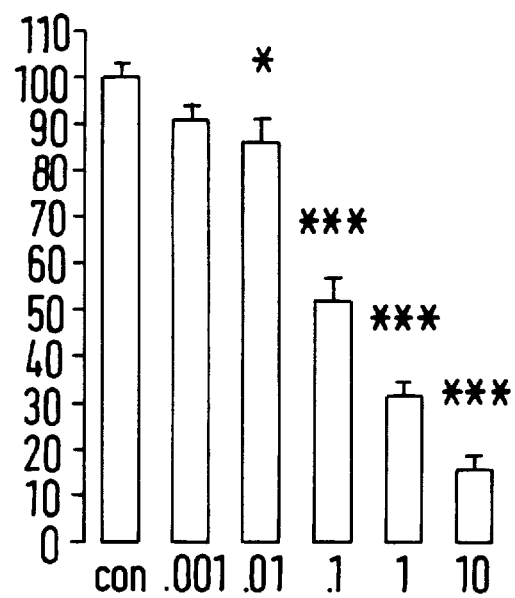

PHARMACEUTICAL CONTROL OF INFLAMMATION

CROSS-REFERENCE TO RELATED APPLICATIONS

The present application is a continuation-in-part (CIP) of International Application No. PCT/GB95/02249, filed Sep. 22, 1995, which disclosure is herein incorporated by reference.

BACKGROUND OF THE INVENTION

1. Field of the Invention

This invention relates to the control of the inflammatory response, to pharmaceuticals that inhibit or decrease inflammation, to pharmaceuticals that promote, induce or increase inflammation and to treatment of disease states by inhibiting or promoting inflammation. In particular, this invention relates to control of the activity or the amount or both the activity and the amount of heme-oxygenase in the body.

This invention finds in addition to other applications, particular application in the treatment of diseases manifested in or exacerbated by an inflammatory response (such as in the treatment of chronic inflammatory diseases, for example, rheumatoid arthritis), in humans suffering hypersensitivity reactions such as in asthma, in humans suffering conditions in which ROS (Reactive Oxygen Species) have a pathogenic role such as reperfusion injury and atherosclerosis and, in humans having immunosuppressed states resulting from drug treatments or from pathologies such as AIDS.

2. Related Art

Chronic inflammatory diseases place a heavy social and economic burden on the resources of many nations, but the number of safe and effective treatments is limited. To date, the major research effort has concentrated on those mediators responsible for the initiation and maintenance of the pathological process. In contrast little attention has been focused on endogenous factors responsible for the resolution of the inflammation.

The main anti-inflammatory pharmaceutical agents are the glucocorticoids and the non-steroidal anti-inflammatory drugs (NSAIDs). Both suffer from well catalogued disadvantages, indeed nearly one quarter of adverse drug reactions reported in the UK are due to NSAIDs. Side-effects of NSAIDs commonly affect the gastrointestinal tract, and also the liver, kidney, spleen, blood and bone marrow. NSAIDs are not effective in treatment of some chronic inflammatory disorders.

Glucocorticoids are powerful anti-inflammatory agents, suppressing both acute and chronic phases of inflammation. They carry the hazard, however, that they also suppress the immune response and can decrease many aspects of essential cell repair processes. Generally, they must be given by injection and are not effective on oral administration.

There thus exists an on-going need for further anti-inflammatory drugs, which can be given orally and which are effective against chronic inflammation.

Conversely, a number of diseases are known in which there is a significant suppression of the inflammatory response. One example is acquired immune deficiency syndrome (AIDS) in which infection by HIV leads typically to such immuno-suppression that an infected person dies from a separate, opportunistic, infection, often a bacterial or viral infection rarely fatal in a healthy person. Stimulation or induction of inflammation in this case could assist in preventing death from non-HIV infections. However, no suitable pharmaceutical is known for this pro-inflammatory purpose.

Heme (ferri-protoporphyrin-IX) plays a vital role in cellular metabolism, functioning as the prosthetic group of hemeproteins (e.g., hemoglobin and cytochromes). It's catabolism is a two-step process. The first, and rate limiting reaction, is the production of biliverdin and carbon monoxide by the microsomal enzyme heme-oxygenase. The second step is the production of bilirubin from biliverdin by the cytosolic enzyme, biliverdin reductase.

Heme-oxygenase is found in liver, kidney, spleen and skin, and has also been localized to specific cell types, notably fibroblasts and macrophages. The enzyme exists in at least two isoforms, one constitutive and the other inducible. Heme, heavy metal ions (e.g., tin, gold, platinum and mercury) and transition metal ions (e.g., iron, cobalt, chromium and nickel) can all induce heme-oxygenase. In addition, heme-oxygenase is induced as part of a generalized stress response to stimuli such as thermal shock (hence the alternative name heat-shock protein 32; hsp32), oxidative stress and cytokines such as interleukin-1 (IL-1), tumor necrosis factor and IL-6. The stress response is seen as beneficial in that it results in protection of vulnerable cell enzymes from inactivation.

Animal biles have been used in traditional Chinese medicine for centuries in the treatment of bronchitis, asthma and other hypersensitivity reactions. More recently, it has been shown that biliverdin and bilirubin scavenge reactive oxygen species (ROS) which can have a range of proinflammatory effects including inactivation of protease inhibitors, depolymerization of hyaluronic acid to angiogenic fragments and alteration of proteins to give rise to endogenous antigens.

Heat shock proteins (HSPs) or stress proteins are a group of proteins that are among the most highly conserved and abundant proteins in the biosphere. Although many of the isoforms of the proteins are expressed under normal physiological conditions and serve vital roles in the cell, they are greatly upregulated by factors which threaten the integrity of the cell. These factors include heat and cold shock, oxygen radicals, heavy metals, hypoxia, infection, ethanol, ionophores and thiol reactive agents. This increase in the cell's concentration of HSPs leads to the cell being transiently resistant to an otherwise lethal insult, and unresponsive to some biological mediators.

The role of HSPs in pathological conditions has attracted much attention. Immune responses to HSPs can be highly cross-reactive and even auto-reactive due to their extensive inter-species amino acid homology. Immune responses to HSPs have already been implicated in adjuvant arthritis in the rat, pristane arthritis in the mouse, diabetes mellitus in the non-obese diabetic mouse, rheumatoid arthritis, systemic lupus erythematosus, atherosclerosis and in tumor surveillance. Therefore, it appears that HSPs may have a paradoxical effect in pathological conditions, having a cytoprotective effect on cells and tissue in stressful environments, but eliciting a detrimental immune response in some autoimmune diseases.

Nitric oxide (NO), formed from L-arginine and molecular oxygen by isoforms of the enzyme nitric oxide synthase (NOS EC 1.14.13.39), is involved in a variety of physiological and pathophysiological processes. The reactivity of this molecule and its capacity to complex with metalloproteins, underlies many of its biological actions. For example, activation by NO of heme-containing soluble guanylate cyclase (EC 4.6.1.2) in vascular smooth muscle results in vasoregulation, whilst in host defence, inhibition of iron-sulphur enzymes causes metabolic dysfunction in invading pathogens.

Inflammation involves the sequential release of various mediators including vasoactive mediators, chemoattractants, cytokines, prostaglandins, free radicals and proteases. In rheumatoid arthritis, a chronic inflammatory disease, HSPs are upregulated in the synovial lining of patients. However, their role in inflammation has yet to be completely elucidated.

Abraham et al., *Int. J. Biochem.* 20(6): 543–558 (1988) provides a general review of heme-oxygenase and its role in mammalian physiology including regulation of its activity by endogenous and exogenous factors. The interaction of this enzyme with NADPH-cytochrome P450 reductase is discussed, as is the role of heavy metal ions in inducing heme-oxygenase activity. Metal Porphyrins are taught as inhibitors. At p. 548 of the reference, the author states:

In general, heme-oxygenase activity increases when cells are under stress or in a disease state. In fact, the enzyme may be regarded as a red light signaling the occurrence of abnormality.

Sacerdoti et al., *Science* 243:388–390 (1–20–89) asserts that hypertension was linked to kidney cytochrome P450 levels, and that enzyme could be depleted by inducing heme-oxygenase production. This was done by treatment with $Co^{2+}$.

McCarty (*Chemical Abstract*, 100:1864024 (1984)) purports to teach the effect of selenium in reducing leukotrienes which are alleged to be prominent mediators of hypersensitivity and inflammation. McCarty, in fact, teaches the administration of a dietary adjuvant per os.

U.S. Pat. No. 5,102,670 relates to the reduction of ocular swelling by administering a heme-oxygenase inducer to the swollen eye of an individual to increase production of heme-oxygenase to reduce the amount of 12(R) hydroxyeicostetraenoic acid (12(R)-HETE) present in the eye as well as 12(R) Dihydroxyeicosatrienoic acid (12(R)-DIHETE) also present in the eye. The scheme presented in the patent for reducing corneoconjunctival swelling is thus dependent on the reduction of the arachidonic acid metabolites 12(R) HETE and 12(R)DIHETE found mainly in the eye. In particular, it is explained that the therapeutic effect is primarily on maintaining the blood—aqueous barrier, a barrier not seen other than in the eye. Thus, the teachings in the patent relate solely to the eye and have very little other applicability.

During about the same time period Messrs. George S. Drummond and Hallah Kappas of The Rockefeller University, Drummond, N.Y. were involved together and with others in research relating to heme-oxygenase. The result of the research appears embodied, at least in part, in U.S. Pat. Nos. 4,657,902; 4,699,903; 4,684,637; 5,010,073 and 5,223,494.

U.S. Pat. No. 4,657,902 purports to teach the use of the novel compound tin mesoporphyrin and compositions containing it to inhibit heme metabolism in mammals, to control the rate of tryptophan metabolism in mammals, and to increase the rate at which heme is excreted by mammals.

The patent disclosure provides as follows at Column 1, lines 22–36:

In mammals and other vertebrates heme is oxidatively degraded by heme-oxygenase to form the open chain tetrapyrrole biliverdin. In mammals biliverdin is reduced to bilirubin by biliverdin reductase. In liver bilirubin is converted to the mono- and di- glucuronide conjugates by the hepatic glucuronyl transferase system prior to its excretion.

Bilirubin is a toxic compound, but normally this toxicity is not manifest since bilirubin is rapidly bound to plasma proteins, transported to liver, conjugated and excreted. However, in the newborn, high undesirable concentrations of bilirubin exist in serum and may produce neurotoxicity. The intractable neurological syndrome known as "kernicterus" is the most severe manifestation of bilirubin toxicity.

The inventors, therefore, provide at column 3, lines 43–48:

It has now been discovered that the compound Sn(tin)-mesoporphyrin (SnMP) can be employed in the treatment of mammals including humans in need of such treatment to decrease the rate of heme metabolism, to increase the rate at which heme is excreted and to control the rate of tryptophan metabolism in the liver.

U.S. Pat. No. 4,699,903 purports to teach a method of increasing the rate at which heme is excreted by a mammal in need of increased disposal of heme by administering tin diiododeuteroporphyrin.

U.S. Pat. No. 4,684,637 discloses methods for decreasing the rate of metabolism for decreasing the rate of metabolism of heme in mammals by administration of tin or chromium protoporphrins IX.

U.S. Pat. No. 5,010,073 purports to relate to liposomal metalloporphyrin preparations for targeting the spleen for inhibition of heme-oxygenase activity in the spleen.

U.S. Pat. No. 5,223,494 purports to teach a method for inhibiting heme-oxygenase activity in the intestine by administering mesoporphyrin for reducing the absorption of iron from foodstuffs by animals in need of such prevention.

This latter group of patents relates to inhibiting heme-oxygenase in selected body tissues by targeting those body tissues (for example, the spleen or intestine) for specified purposes.

SUMMARY OF THE INVENTION

Objects of this invention are to provide improved (or at least alternative) means for control of inflammation, in particular treatment of chronic inflammation or stimulation of an inflammatory response, such as in treatment of an immunosuppressed condition.

By controlling the amount or the activity or both the amount and the activity of heme-oxygenase in the body, either (1) a generalized anti-inflammatory effect or response is obtained wherein heme-oxygenase is induced, or (2) a general inflammatory response is obtained wherein heme-oxygenase is suppressed (or inhibited).

This invention provides a method of control of inflammation, comprising administering to a mammal an effective amount of a compound that alters activity, or amount, of heme-oxygenase.

This invention also provides a method for treatment of inflammation comprising administering, to a mammal, an effective amount of a compound that increases heme-oxygenase activity in the mammal.

This invention further provides a method for treatment of inflammation comprising administering to a mammal a compound that induces heme-oxygenase in order to treat inflammation.

This invention also provides a pharmaceutical composition for the treatment of inflammation, comprising a compound that increases heme-oxygenase activity, selected from the group consisting of a tablet, a pill, a powder for suspension in aqueous solution, a powder for dissolution in aqueous solution, a topical preparation further comprising an oil, a wax, a gel, a cream, an emulsion, and a sterile aqueous solution for injection.

This invention also provides a pharmaceutical composition for treatment of inflammation comprising a compound that increases heme-oxygenase activity selected from the group consisting of a prostaglandin of the A series; an agonist of a prostaglandin A receptor; vitamin $B_{12}$; hemin; and a fragment, sub-unit, conjugate, analogue, derivative or complex of hemin retaining heme-oxygenase inducing activity.

This invention further provides a pharmaceutical composition for the treatment of inflammation comprising a taste enhancing agent and being for oral administration.

This invention also provides a method of treatment of chronic inflammation, comprising administering to a mammal an effective amount of a compound that increases heme-oxygenase activity.

This invention further provides a method of treatment of a disease selected from rheumatoid arthritis, a chronic inflammatory bowel disease, multiple sclerosis, asthma, airways inflammatory disease, tendonitis and chronic inflammation in the brain, comprising administering to a mammal an effective amount of a compound that increases heme-oxygenase activity.

This invention also provides a method of stimulating an inflammatory response, comprising administering to a mammal an effective amount of a compound that decreases heme-oxygenase activity.

This invention further provides a method of stimulating an inflammatory response comprising administering a heme-oxygenase inhibitor.

This invention also provides a method of stimulating an inflammatory response comprising administering a heme-oxygenase inhibitor that is a structural analogue of FePP that inhibits heme-oxygenase.

This invention further provides a method of stimulating an inflammatory response comprising administering a heme-oxygenase inhibitor that is a structural analogue of FePP that inhibits heme-oxygenase, wherein the analogue is selected from SnPP, SnMP, SnDPP, CrPP, CrMP, CrDPP, ZnPP, ZnMP, ZnDPP, MnPP, MnMP, MnDPP, wherein PP equals protoporphyrin, MP equals mesoporphyrin and DPP equals diiododeuteroporphyrin.

This invention also provides a method of treating immunosuppression, comprising administering to a mammal an effective amount of a compound that decreases heme-oxygenase activity.

This invention further provides a method of treating immunosuppression for treatment of AIDS.

This invention also provides a method of stimulating an inflammatory response comprising administering a heme-oxygenase inhibitor that is a structural analogue of FePP that inhibits heme-oxygenase for stimulation of mononuclear cells.

BRIEF DESCRIPTION OF THE FIGURES

FIG. 6: Analysis of inflammatory cell pellet for HO-1. Lanes, inflammatory cells taken at 2, 6, 12, 24 and 48 hours, spleen homogenate (SP), PBL (BL).

FIG. 7: Analysis of inflammatory cell pellet for HO-2. Lanes, inflammatory cells taken at 2, 6, 12, 24 and 48 hours, brain homogenate (BR), PBL (BL);

FIG. 8: Normal rabbit serum (control); FIG. 9: 6 hour inflammatory cell smear; FIG. 10: 48 hour inflammatory cell smear;

FIGS. 23 and 24 are graphs that show the effect of sodium nitroprusside on rat brain and spleen heme-oxygenase activity, FIG. 23—brain homogenates, FIG. 24—spleen homogenates. 0.001, 0.01, 0.1, 1 or 10 mM sodium nitroprusside was incubated with reaction mixture, results are expressed as a percentage of control (Con) group which received no compound, n=8, * P<0.05,  P<0.01, * P<0.001.

DETAILED DESCRIPTION OF THE PREFERRED EMBODIMENTS

Figure 1:
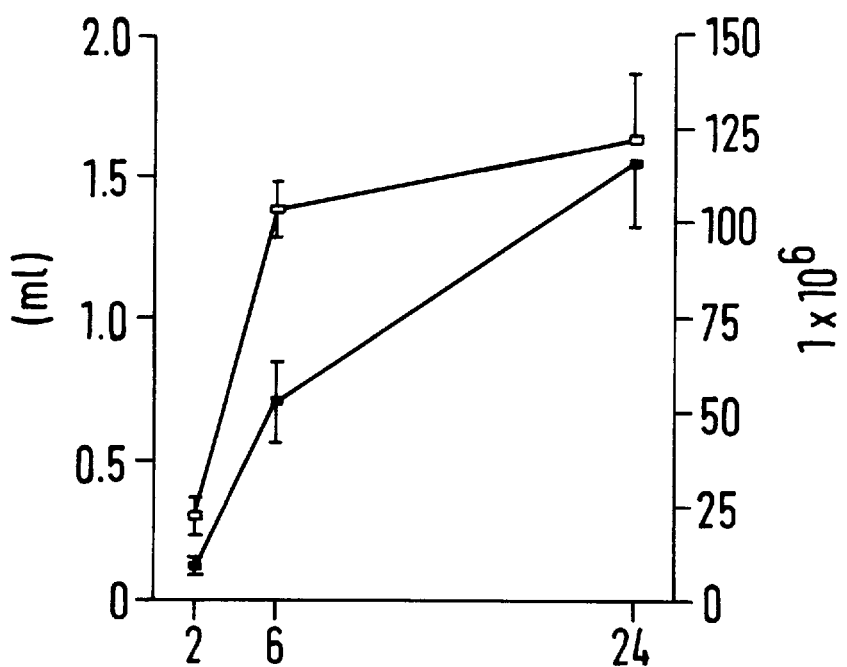
FIG. 1 is a graph that illustrates the development of an acute inflammation at 2, 6 and 24 hours after injection of carrageenin into the rat pleural cavity (open boxes—Cell exudate, closed boxes—Total cells, n=6 each time point)

According to one aspect of the invention, inflammation is treated by administration of a compound that induces heme-oxygenase or stimulates or increases the activity of heme-oxygenase. The treatment can be systemic or targeted, for example targeted to an inducible heme-oxygenase found in monocytes and macrophages in the human body. This treatment induces heme-oxygenase production and/or stimulates its activity; specific medical applications include the treatment of chronic inflammatory diseases for example, rheumatoid arthritis, the treatment of hypersensitivity reactions such as in asthma, and, the treatment of injury, atherosclerosis and infarction.

In an embodiment of the invention, a pharmaceutical composition comprises a compound that induces, stimulates or increases the activity of heme-oxygenase, in combination with a pharmaceutically acceptable carrier. The composition is in the form of a solution for injection, an orally acceptable composition or a topical composition.

A suitable solution for injection includes a sterile, saline-containing solution, preferably containing saline at approximately physiological concentration.

For oral administration, the composition can be in a solid form-such as a tablet, a pill or a powder for suspension in water or for dissolution in water. The preparation of such a solid composition will be known to a person of skill in this art. See *Remington's Pharmaceutical Sciences*, 18th Edition, Mack Publishing Company, Easton, Pa. (1990). It is an option to supplement the oral composition with a taste enhancing agent, to make the composition more palatable, or at least less unpleasant by mouth. Suitable taste enhancers includes sweeteners, flavorings and agents that mask or reduce any unpleasant or undesirable taste in the active component of the pharmaceutical.

In the case of a topical composition, the carrier is preferably a non-aqueous carrier adapted to retain the composition in place following application. Suitable carriers include a cream, a gel, a wax, an oil and an emulsion.

The invention thus provides a further anti-inflammatory pharmaceutical. It can be given orally, according to the particular compound chosen, and initial tests have demonstrated useful anti-inflammatory activity. The products of heme-oxygenase are believed to have multiple effects in the progression of inflammation, whereas the products of the enzyme targeted by most NSAIDs, cycloxygenase, have fewer effects, so the compositions of the invention present a pharmaceutical activity potentially more powerful than that seen in NSAIDs.

Another embodiment of the invention is an anti-inflammatory composition comprising a heme-oxygenase inducer or stimulator and a pharmaceutically acceptable carrier.

A further embodiment of the invention is the use of a compound that induces, stimulates or increases the activity of heme-oxygenase in the manufacture of a medicament for the treatment of inflammation.

Agents suitable for inducing heme-oxygenase include prostaglandins of the A series; analogues, derivatives, complexes and conjugates of prostaglandins of the A series that are agonists of prostaglandin A receptors; agonists of prostaglandin A receptors; vitamin $B_{12}$; hemin; and fragments, sub-units, conjugates, analogues, derivatives and complexes thereof that retain heme-oxygenase inhibiting activity. Suitable dosage amounts are from 0.1 to 30 µmoles/kg of body weight of for example, a human. For example, where hemin (FePP) is used, suitable dosage amounts would be from about 0.06 mg hemin to about 24 mg hemin per kilogram of body weight.

Alternative agents for induction or activation of heme-oxygenase are agents that inhibit or decrease nitric oxide synthesis. We have discovered a substantially reciprocal relationship between nitric oxide (NO) levels and heme-oxygenase activity wherein decreasing NO levels results in an increase in HO activity, and is anti-inflammatory. Thus, another embodiment of the first aspect of the invention is a pharmaceutical composition comprising, as an active ingredient, a substance that decreases NO levels, such as an inhibitor of nitric oxide synthetase (NOS).

According to a still further embodiment of the invention, a method of inducing (increasing) the level of heme-oxygenase in the body of a patient is provided, said method comprising administration of an effective dosage amount of heme-oxygenase inducer to reduce the inflammatory response in the patient.

In specific embodiments of the invention, inflammation is treated by inducing or stimulating a heme-oxygenase in mononuclear cells, such as in particular an inducible heme-oxygenase found in monocytes and macrophages. This is advantageous when treating chronic inflammation, typically medicated by and characterized by a large population of these cells at an inflammation site. According to another embodiment of the invention, a method of controlling the inflammatory response in the human body is provided, said method comprising reducing the inflammatory response by administration of an effective dosage amount of heme-oxygenase inducer.

Preferably, the inducer is administered in a suitable pharmaceutically acceptable vehicle in any suitable manner (for example, sterile water, saline (sterile)). A buffered, isotonic aqueous solution having a pH of between about pH7 and pH8 is suitable. Lyophilized preparations are also be suitable. The lyophilized preparations may be reconstituted with sterile water.

In preferred embodiments of the invention, specifically chronic inflammation is treated. Diseases comprising chronic inflammation that can be treated according to the first aspects of the invention include chronic inflammatory joint disease—e.g., rheumatoid arthritis, chronic inflammatory bowel disease—e.g., Crohn's disease, respiratory inflammatory disease—e.g., asthma, chronic inflammation of the brain—e.g., multiple sclerosis, and inflammation of soft tissues—e.g., tendonitis.

According to another embodiment of the invention, a method of reducing the inflammatory response in the human body generally (treating inflammation) is provided, the method comprising monitoring the presence (expression) of HSP32 isoform of heme-oxygenase and, if decreased below normal level, administering an effective dosage amount of heme-oxygenase inducer to increase expression of the heme-oxygenase enzyme to thereby reduce the inflammatory response (inflammation). The inducer is preferably targeted at monocytes and macrophages.

Dosage amount(s) can be given over a period of time. However, the effects of compounds used to date appear to peak 24 hours after administration of each dosage amount and regress at 48 hours after administration.

The formulation can be in a unit dosage form (for one dosage) or may be packaged as a multiple formulation composition from which suitable dosage amounts can be extracted and used. For example, a solution in a vial may provide the multiple formulation composition from which the dosage amounts can be taken and administered. Compositions and uses of the first aspect of the invention are optionally supplemented by one or both of (1) a NSAID, and (2) a NOS (nitric oxide synthetase) inhibitor.

According to a second aspect of the invention, there is provided stimulation of an inflammatory response by inhibition or suppression of heme-oxygenase. In an embodiment of the second aspect, a pharmaceutical composition for stimulating or enhancing inflammation comprises a heme-oxygenase inhibitor and a pharmaceutically acceptable carrier.

The expressions "stimulate inflammation" and "enhance inflammation" are intended to indicate that at least one characteristic feature of inflammation is stimulated or enhanced; likewise the expressions "suppress inflammation", "decrease inflammation" and variants of all these expressions.

In treatment of immunosuppression using a composition according to the second aspect of the invention, for example treatment of AIDS, a heme-oxygenase inhibitor is administered to stimulate activity of monocytes and/or macrophages. These two cell types are crucial to fighting bacterial and viral infections, so increasing their activity offers a novel therapy, e.g. for AIDS suffers.

Agents suitable for inhibiting heme-oxygenase (for example, inducible heme-oxygenase in monocytes and macrophages) are typically analogues of FePP (nb. which induces heme-oxygenase) in which the Fe ion is replaced by another metal ion, or the PP is replaced. Examples are:

| SnPP | SnMP | SnDPP | CrPP | CrMP | CrDPP |
| ZnPP | ZnMP | ZnDPP | MnPP | MnMP | MnDPP | where:

Sn=tin, Cr-chromium, Zn=zinc, Mn=manganese, PP=protoporphyrin,

MP=mesoporphyrin and DPP=diiododeuteroporphyrin

Suitable dosage amounts of these agents would range from 0.1 to 50 μmoles/kg of body weight of for example, a human. For example, where tin protoporphyrin (SnPP) is used, suitable dosage amounts of SnPP would be from 0.07 mg/kg to 46 mg/kg of body weight of a human.

Antagonists of prostaglandin A receptors are further agents suitable for decreasing heme-oxygenase activity.

Alternative agents for reducing HO activity are agents that increase NO levels. Thus, another embodiment of the second aspect of the invention is a pharmaceutical composition comprising, as an active ingredient, a substance that increases the level of NO in a patient. The substance is, optionally, a substrate for nitric oxide synthetase (NOS) or a stimulator of this enzyme. A known substrate for NOS is L-arginine and a known NO donor is sodium nitroprusside.

According to another embodiment of the invention, a method of reducing the level of heme-oxygenase in the body is provided, said method comprising administration of an effective dosage amount of heme-oxygenase inhibitor to decrease the inflammatory response, for example, targeting an inducible heme-oxygenase found in monocytes and macrophages.

According to a further embodiment of the invention, a method of controlling the inflammatory response in the human body is provided, said method comprising activating the inflammatory response by administration of an effective dosage amount of heme-oxygenase inhibitor, for example, one that targets an inducible heme-oxygenase found in monocytes and macrophages.

The inhibitor can be administered in any suitable pharmaceutically acceptable vehicle in any suitable manner (for example, sterile water, saline (sterile)). A buffered isotonic aqueous solution having a pH of between about pH7 and pH8 is suitable. Lyophilized preparations may also be suitable. The lyophilized preparations may be reconstituted with sterile water and administered.

According to another embodiment of the invention, a method of increasing an inflammatory response is provided (such as for a person suffering from AIDS), the method comprising monitoring the presence (expression) of HSP32 isoform of heme-oxygenase and, if increased above normal level, administering an effective dosage amount of heme-oxygenase inhibitor, thereby to increase the inflammatory response.

Dosage amount(s) can be given over a period of time. However, the effects of compounds used to date appear to peak 24 hours after administration of each dosage amount and regress at 48 hours after administration.

A still further embodiment of the invention is the use of a heme-oxygenase inhibitor in the manufacture of a medicament for treating immunosuppression. Another is the use of a heme-oxygenase inhibitor in the manufacture of a medicament for increasing the activity of monocytes and macrophages.

Immunosuppression can also be caused as a side effect of other therapies, for example post transplant immunosuppression due to drugs designed to suppress rejection of a transplanted organ. Rejection is largely mediated by a T cell response in these circumstances, so immunosuppression is to remove damaging T cell activity. However, a parallel loss of monocyte and macrophage activity (usually due to decreased numbers) is also seen. Thus, another use of the second aspect of the invention is the selective stimulation of monocytes and macrophages. By "selective" it is intended to indicate that activity and/or number of these cells is increased in higher proportion to any increase in activity and/or number of T cells.

The following examples are illustrative, but not limiting, of the method and compositions of the present invention. Other suitable modifications and adaptations of the variety of conditions and parameters normally encountered in clinical therapy and which are obvious to those skilled in the are within the spirit and scope of the invention.

EXAMPLE 1

In the following example, the expression and possible involvement of heme-oxygenase in acute and chronic inflammation was examined. The highly inducible isoform of heme-oxygenase-1 has recently been classified as an HSP (HSP32). This is the rate limiting enzyme in the catabolism of the prosthetic group of heme proteins. The major product of this reaction, bilirubin, is a powerful free radical scavenger and may represent an endogenous mechanism by which cells protect themselves from free radical damage. Carbon monoxide (CO) is also produced by this reaction. Due to the structural similarities to nitric oxide a major mediator of inflammation, and the ability of both molecules to bind heme proteins the role of CO in inflammation raised an intriguing question for which we sought an answer.

In this embodiment, the rat carrageenin pleurisy model of acute inflammation has been used to determine the expression and activity of HSP32 in inflammatory cells. Markers of inflammation, cell exudate and cell number progressively increased over 2, 6 and 12 hours peaking at 24 and regressing at 48. The inflammation was dominated by polymorphonuclear leucocytes (PMNs) at the early time points, with an increase in the monocyte population as inflammation progressed. The increase in monocytes was associated with an increase in HSP32 protein levels determined by Western blot analysis, intensely labeled bands at 24 and 48 hours. Immunohistochemistry confirmed that HSP32 protein was present in monocytes. Heme-oxygenase (HO) activity was also assayed at 2, 6 and 24 hours, the later time point being the only one to show activity. The effects of modulating HO activity with hemin (an inducer of HSP32 expression) and tin Protoporphyrin-IX (synthetic analogue of heme which inhibits HO activity) was then examined. The inducer or the inhibitor had no significant effect on inflammation at 6 hours compared to controls. However, at 24 hours the inhibitor significantly increased cell exudate by 135% (p<0.001 Mann-Whitney), whereas the inducer of HSP32 decreased cell exudate and total cells by 83% (p<0.001) and 50% (p<0.001) respectively. The effects of these compounds thus corresponds to the temporal expression of HSP32 in this model of acute inflammation.

Methods

Male Wistar rates 200±20 grams (Tuck & Sons Ltd., Essex, UK) were used for inflammation. Animals were administered either with 15 mg/kg Ferriprotoporphrin IX chloride (FePP) by intravenous injection—18 hours before inflammation or with 2 doses of 40 $\mu$moles/kg Tin protoporphyrin dichloride (SnPP) by sub-cutaneous injection—18 hours and at the time of inflammation induction (porphyrins were obtained from Porphyrin Products Inc., Logan, Utah). Drugs were prepared in 0.1N NaOH and mixed 1:1 with saline, these were then adjusted to pH 7.4, drug vehicle. The total volume injected was 0.2 ml. Control animals received vehicle only.

Carrageenin pleurisy was induced in rats and cell pellet prepared as previously described by Tomlinson et al.

HO Activity in the cell pellets was measured in post mitochondrial supernatant by quantifying the generation of bilirubin (Jollie D. R., et al., Arch Biochem Biophys, 240, pages 51–59 (1985)), biliverdin reductase was substituted with rat hepatic cytosol (3 mg/ml). Protein was estimated by the Bradford method using BSA as standard.

Cell pellets were lysed by the addition of protease inhibitory buffer containing 1% Triton X100 and boiled (10 min.) with gel loading buffer (Tris, 50 mM; SDS, 10%; glycerol, 10%; 2-mercapthoethanol, 10% bromophenol blue, 2 mg/ml) in a ratio of 1:1 and centrifuged at 10,000 g, for 10 min. The protein concentrations of supernatants were determined as above, and total protein equivalents (20 $\mu$g) for each sample separated on 10% sodium dodecyl sulfide-polyacrylamide mini-gels (Hoefer; Staffordshire, UK) using the Laemmli buffer system and transferred to polyvinylidene difluoride membranes (Millipore, Hertfordshire, UK). Non-specific IgGs were blocked with 5% dried milk protein and incubated with a polyclonal antibody to HSP32 1:1000 dilution (Stressgen Crop., Victoria, Canada). Bands were detected with an amplified alkaline phosphatase kit (Sigma Co. Poole, UK) and developed with nitroblue tetrazolium (NBT)-5-bromo-4-chloro-3-indonyl phosphate (BCIP). Rainbow marker and pre-stained blue protein markers were used for molecular weight determinations.

Results are expressed as the mean ± s.e. mean. Statistical analysis was determined by Mann-Whitney U-test, with a P value of <0.05 considered significant.

Figure 2:
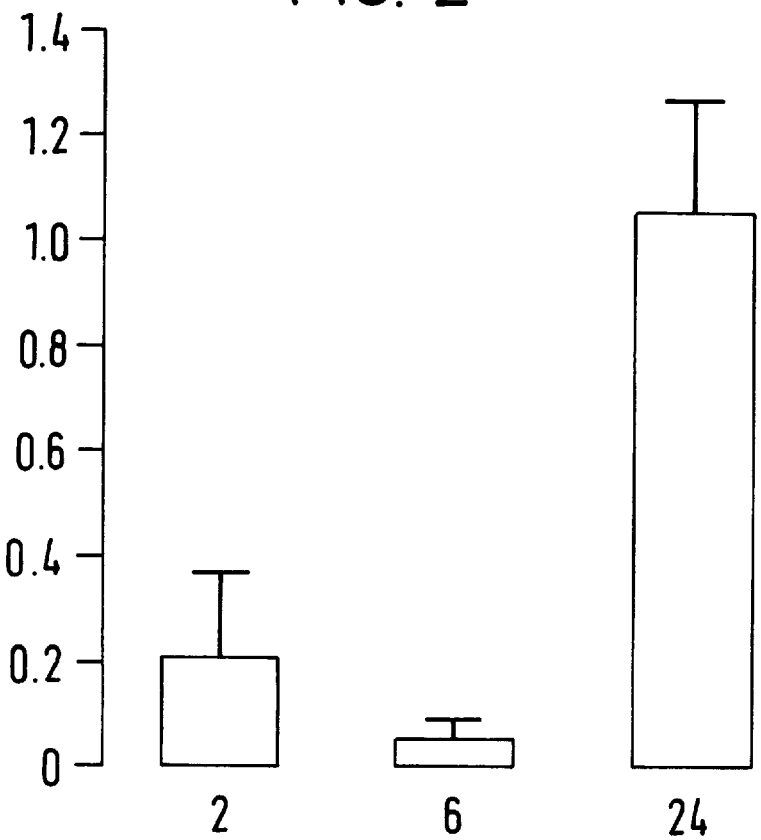
FIG. 2 is a bar graph that illustrates the measurement of HO activity as nmol bilirubin/60'/mg protein against time in hours during acute inflammation (n=6 each time point)
Figure 3:
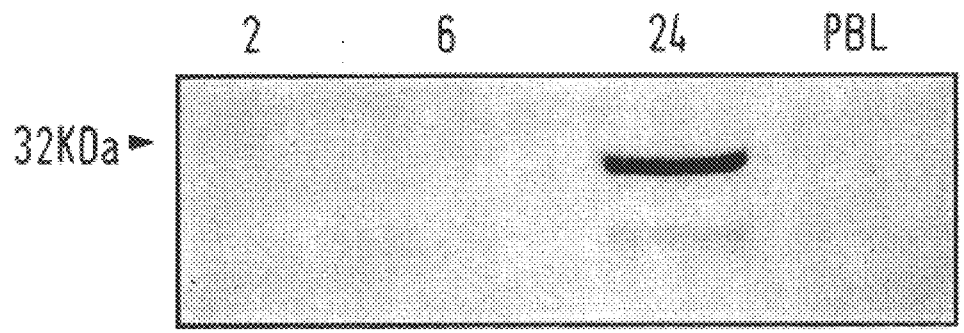
FIG. 3 is a photograph showing HSP detection by Western blot analysis, with a peak at 24 hours.

FIG. 1 shows the development of exudate volume and cell number during inflammation in the pleural cavity; these were both maximal 24 hours after injection of the carrageenin. A significant increase in HO activity in the exudate cell pellet, FIG. 2, and the detection of HSP32 protein by western blot analysis, FIG. 2, and FIG. 3 (photo), coincided with this peak in inflammation. The effects of the HO inhibitor SnPP and inducer FePP on carrageenin inflammation were then investigated (Table 1). Exudate volumes and cell numbers at 6 hours were not significantly modified by pre-treatment with HO inhibitor or inducer. However, 24 hours after initiation of the inflammation SnPP increased exudate volume by 128% as compared to vehicle control (P<0.001) whereas FePP decreased exudate volume by 73% and cell number by 50% compared to vehicle control (both P<0.001).

The effect of heme-oxygenase inhibitor Tin protoporphyrin dichloride (SnPP) and inducer ferriprotoporphyrin IX chloride (FePP) on acute inflammation was examined. Treatment animals received either 2 doses of 40 $\mu$moles/kg SnPP s.c.—18 and 0 hours before induction of inflammation, or 1 doses of 15 mg/kg FePP i.v—18 before inflammation. Treatment animals were compared to control animals which had received vehicle only by the appropriate route.***P<0.001.

These results demonstrate for the first time the induction of HSP32 expression and HO activity in inflammatory cells from a model of acute inflammation. The increase in HO activity reported above is associated with an increase in macrophages population in the pleural cavity. Immunohistochemistry demonstrated strong positive immunoreactivity of inflammatory macrophages but not peripheral monocytes for HSP32 in this model (data not given). The effect of pre-stimulating or inhibiting HO activity significantly decreases or increases inflammation respectively at 24 hours. This indicates that the major effect of HO modulators is on inflammatory macrophages at 24 hours, with no significant effect at 6 hours when the inflammatory site is dominated by polymorphonuclear leucocytes. An increase in HO activity achieved by the invention represents a novel therapy for the treatment of chronic inflammatory disease and, conversely, a decrease in activity will be of benefit in those individuals with an impaired inflammatory response.

EXAMPLE 2

Methods

Animals received 2 doses of either 3, 10 or 30 $\mu$moles/kg SnPP (a HO inhibitor) or vehicle control—18 hours and at the time of inflammation induction. Animals received 1 dose of either 3, 10 or 30 $\mu$moles/kg FePP (a HO inducer) or vehicle control—18 hours before induction of inflammation, n=9.

Male Wistar rats 200+20 grams were anaesthetized with halothane and 150 ul of a 1% carrageenin solution in 0.9% NaCl injected into the pleural cavity. Exudates were collected 2, 6, 12, 24 and 48 hours after injection of the irritant by pleural lavage with 1 ml protease inhibitory buffer containing: trisodium citrate 3.15%, phenylmethylsulfonyl fluoride 1 mM (Sigma Chemical Co., Poole, UK), pepstatin A 1.5 mM (Sigma) and leupeptin 0.2 mM (Sigma) in 10 mM phosphate buffered (PBS) pH 7.3. Any exudates with blood contamination were rejected. Cells were counted using a Coulter counter, model DN (Coulter Electronics Ltd., Luton, UK). Each sample was centrifuged at 800 g for 10 minutes and the resultant cell pellet prepared as outlined below.

Peripheral blood and exudate cell samples were smeared onto poly-L-lysine coated slides and allowed to air dry. Prior to immunolabeling or histological staining, smears were fixed in 4% paraformaldehyde in 0.1M phosphate buffer for 1 hour. Endogenous peroxidase were quenched with 0.3%

H$_2$O$_2$ in methanol and sections washed with 0.1% Triton X100 in PBS. Non-specific binding of IgGs was blocked using NGS 1:50 in 0.1% essentially globulin free BSA in PBS. The sections were incubated overnight with polyclonal anti-HO-1 (1:200) or polyclonal anti-HO-2 (1:1000) at 4° C., washed and incubated for a further 30 minutes with biotinylated goat anti-rabbit secondary antibody. Following a further 30 minutes incubation with Vectastain ABC horseradish-peroxidase (Vector Labs, Peterborough, UK), the substrate 0.05% diaminobenzidine tetrahydrochloride (Sigma) in 0.05M Tris buffer pH 7.6 was added for the appropriate time period (5–10 mins). This resulted in positive immunoreactivity labeling brown. Primary antiserum was replaced with NGS, as a negative control. Morphological observations were confirmed using the routine histological stain, haematoxylin and eosin.

Results are expressed as the mean ± s.e.mean for (n) experiments. Statistical analysis was determined Student's unpaired t test, with a P value of <0.05 considered significant.

HO activity is assessed as previously described by Sierra E. S., et al.,*Anal. Biochem.* 1992; 200:27–30. Cells are lysed by sonication for 10 seconds in protease inhibitory buffer. Heme-oxygenase is assayed as previously described. The reaction mixture (15 μl) consists of 11.2 μM [$^{14}$C] heme specific activity 54 Ci/mol), 1 mM NADPH, 2 mM glucose-6-phosphate, 0.1 units of glucose-6-phosphate dehydrogenase, 3 mg/ml liver cytosolic protein and 50–100 μg of sample protein. The reaction is started by the addition of the heme, incubated at 37° C. for 30 minutes and stopped by the addition of excess cold heme and bilirubin followed by placing on ice. 2 μl of reaction mixture is spotted twice onto a silica gel thin-layer chromatography sheet. The chromatogram is developed using a 20:1 dilution of chloroform:acetic acid. Spots corresponding to hem and bilirubin are were cut out and placed in 10 ml of scintillation fluid to be counted. Protein determination were carried by the Bradford method (Bradford MM et al,*Anal. Biochem.* 1976; 72:248–254), BSA was used as protein standard. The activity is expressed as pmoles bilirubin/mg protein/hour, n=9. Results are expressed as the mean ± s.e.mean.

Results

Figure 4:
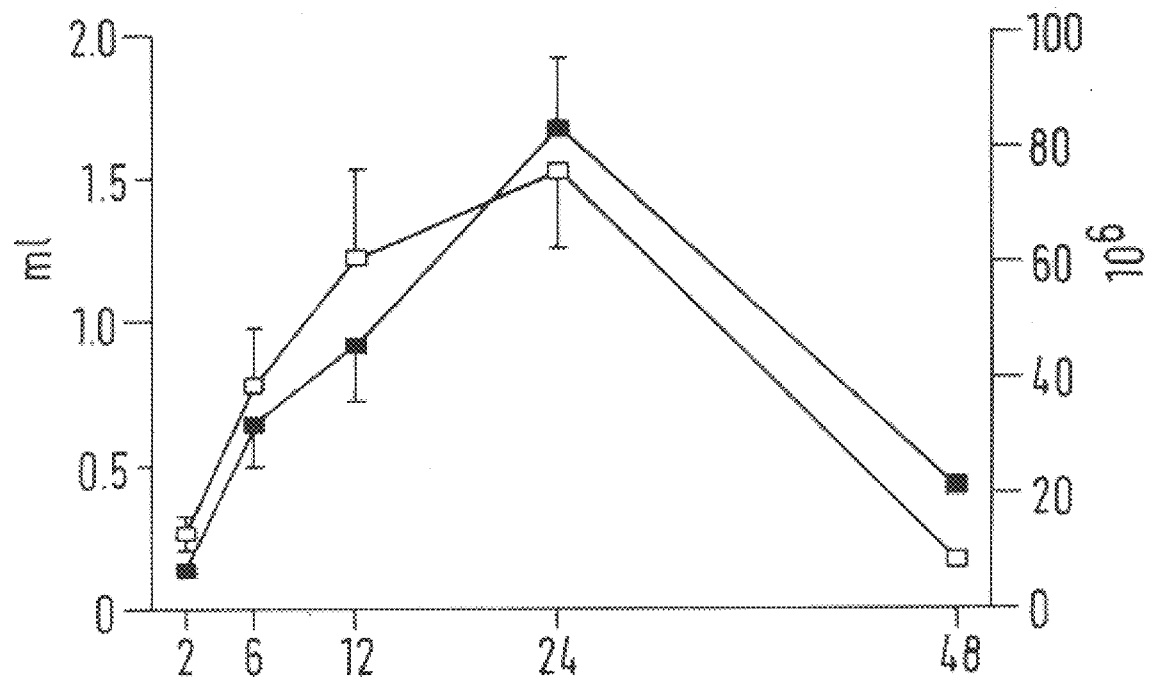
FIG. 4 is a graph that shows the development of acute inflammation in hours after injection of carrageenin into the rat pleural cavity (□ Exudate volume,■ Total inflammatory cells, n=10)
Figure 5:
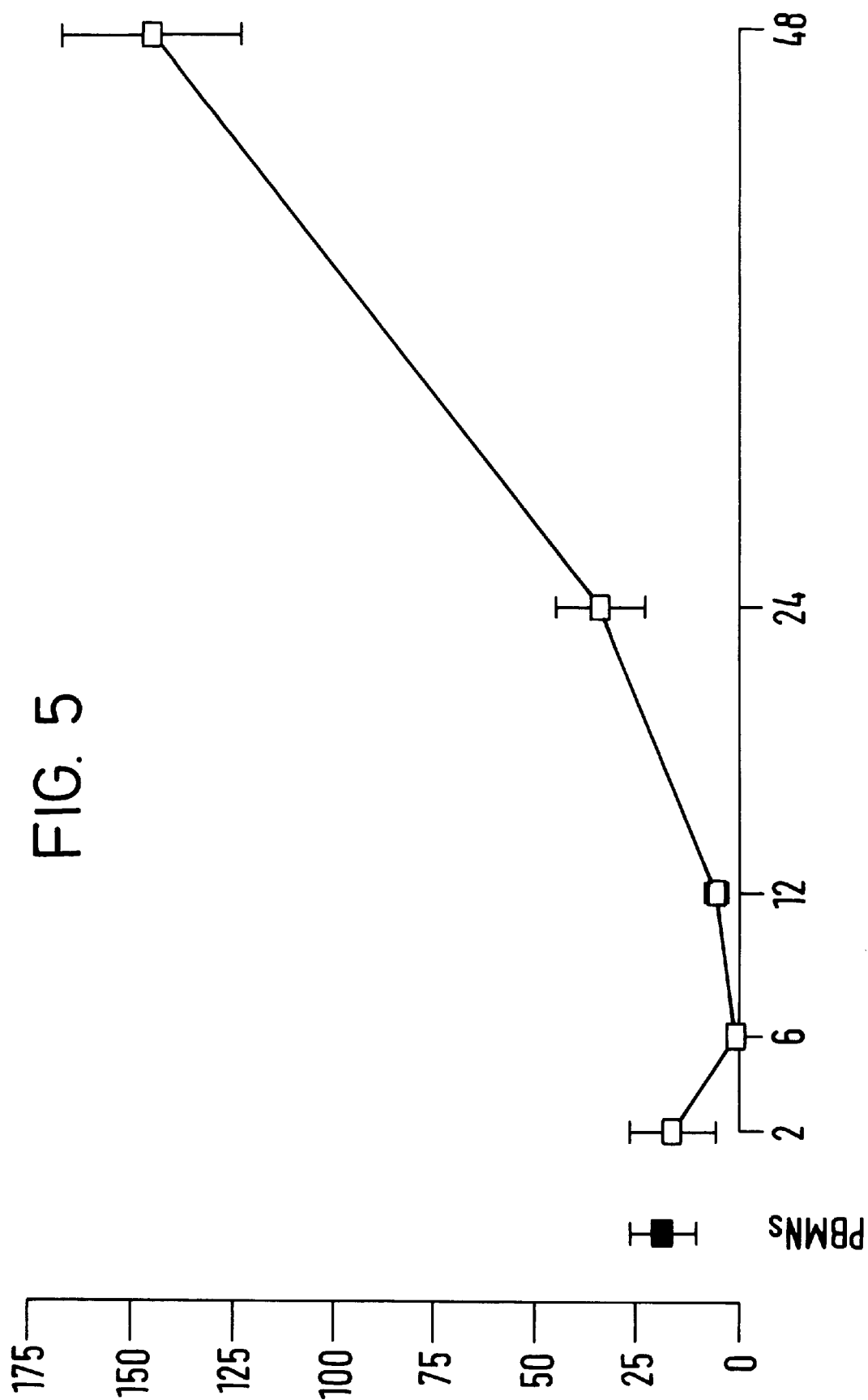
FIG. 5 is a graph that shows heme-oxygenase (HO) activity of inflammatory cells against time (hours) during carrageenin pleurisy, the activity is expressed as pmoles bilirubin/mg protein/hour, n=9 (results are expressed as the mean ± s.e.mean. ■ E Peripheral blood mononuclear cells (PBMNs), □ Time course of inflammatory cells)
Figure 6:
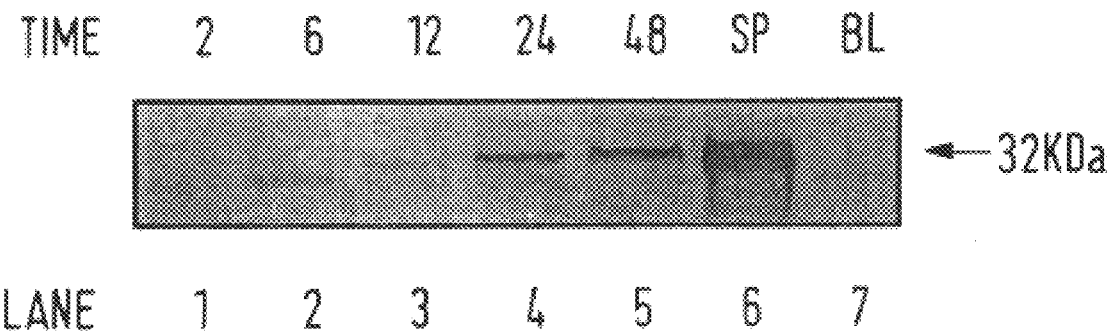
FIGS. 6 and 7 are photographs that show Western blot analysis for heme-oxygenase isoforms.
Figure 7:
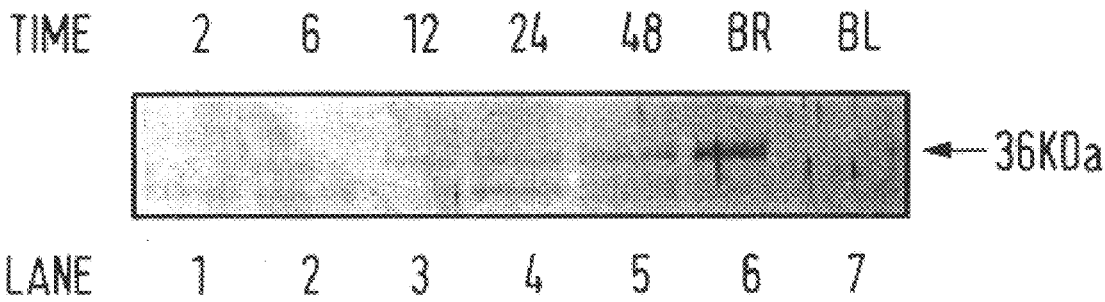
Figure 8:
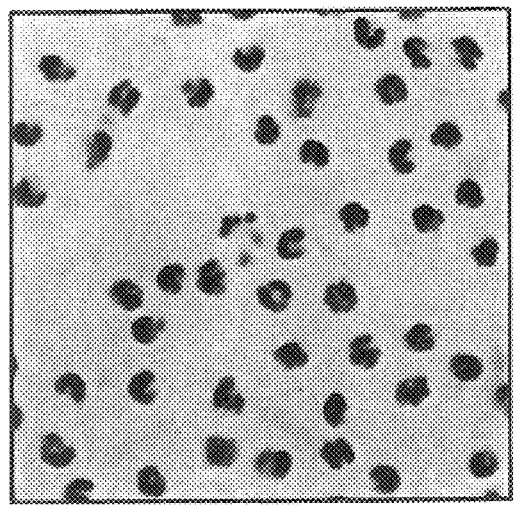
FIGS. 8–10 are photographs that show immunolocalization of inflammatory cell smears for heme-oxygenase 1 confirming increased positive staining for heme-oxygenase-1 protein in mononuclear cells.
Figure 9:
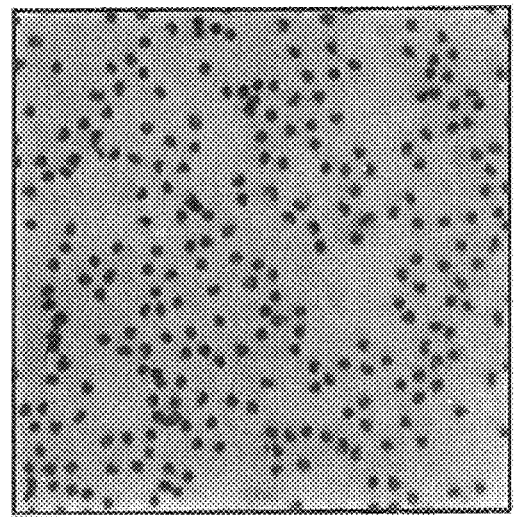
Figure 10:
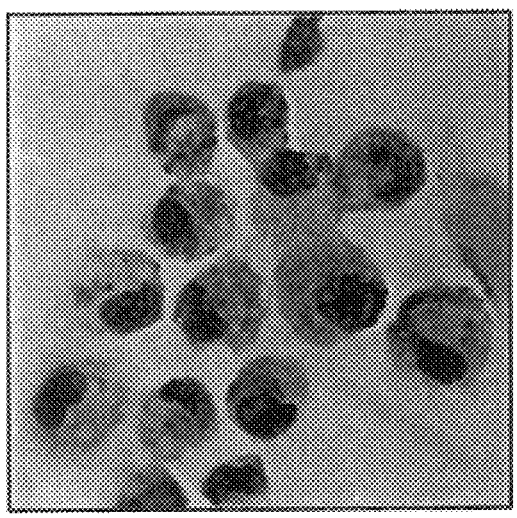

Injection of carrageenin into the pleural cavity of a rat resulted in the development of an acute pleurisy which was maximal at 24 hours as assessed by inflammatory cell number and exudate volume (FIG. 4). At 48 hours the inflammatory lesion had virtually resolved, with cell number and exudate volume reduced to 25% and 11% respectively of levels seen when inflammation was maximal. The early part of the inflammation was characterized by influx of polymorphonuclear cells (PMNs) into the pleural cavity, with an increasing percentage of mononuclear cells (MNs) occurring at 24 and 48 hours [Table 2]. HO activity dramatically increased as the inflammation progressed, the highest activity being recorded when the inflammation was resolving (FIG. 4) when MNs dominated the inflammatory lesion. Western blot analysis confirmed that there was a dramatic increase in HO-1 protein levels (data not shown). In inflammatory cell smears HO-1 immunoreactivity was specifically localized to mononuclear cells with PMNs showing little or no staining. The number of positively stained cells increased as the inflammation progressed (FIGS. 8–10). A similar staining profile with immunoreactivity being localized to mononuclear cells was observed with polyclonal antibodies to HO-2.

These results indicated that there is an increase in HO expression and activity in inflammatory cells. To investigate whether increased HO activity was not only associated with tissue protection but also involved in resolving acute inflammation we used an HO inhibitor, tin protoporphyrin (SnPP), administered sub-cutaneously 18 hours before and at the time of carrageenin injection, and an HO inducer, ferriprotoporphyrin IX chloride (FePP), given sub-cutaneously 18 hours before induction of the inflammation (Maines MD et al., *FASEB J*. 1988; 2:2557–2568).

Figure 11:
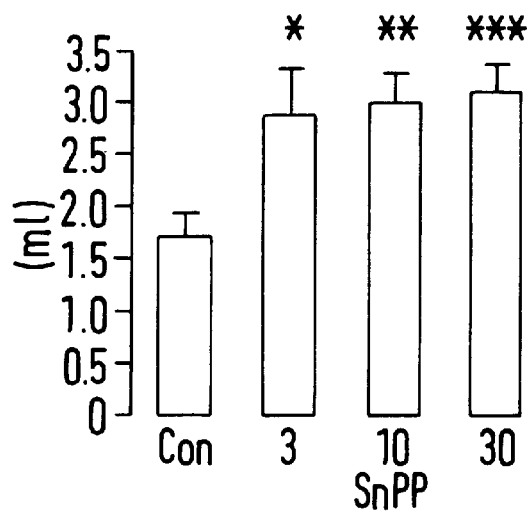
FIGS. 11–16 are bar graphs that show the effect of heme-oxygenase (HO) modulators on inflammation and HO activity: Effect of tin protoporphyrin dichloride (SnPP) on acute inflammation at 24 hours (FIG. 11—exudate volume, FIG. 12—cell number), Effect of ferriprotoporhyrin IX dichloride (FePP) on acute inflammation at 24 hours (FIG. 13—exudate volume, FIG. 14.—cell number), Effect of SnPP (FIG. 15) and FePP (FIG. 16) administration on HO activity in 24 hour inflammatory cells, inflammatory cells were collected after treatment with the above porphyrins and HO activity measured as for FIG. 5, n=6. * P<0.05,  P<0.01 and * P<0.001.
Figure 12:
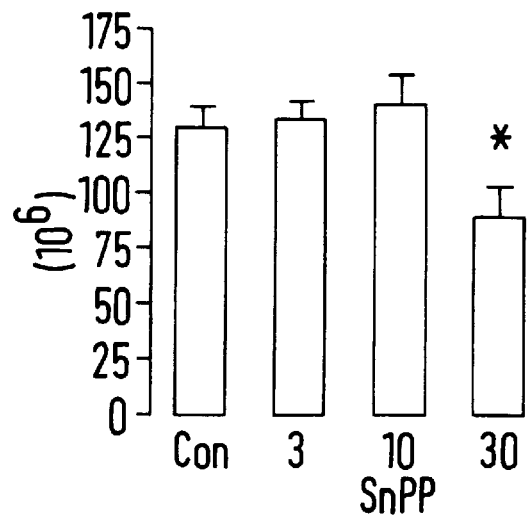
Figure 13:
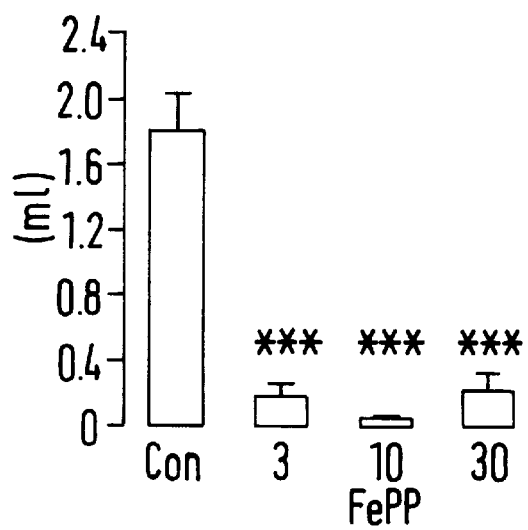
Figure 14:
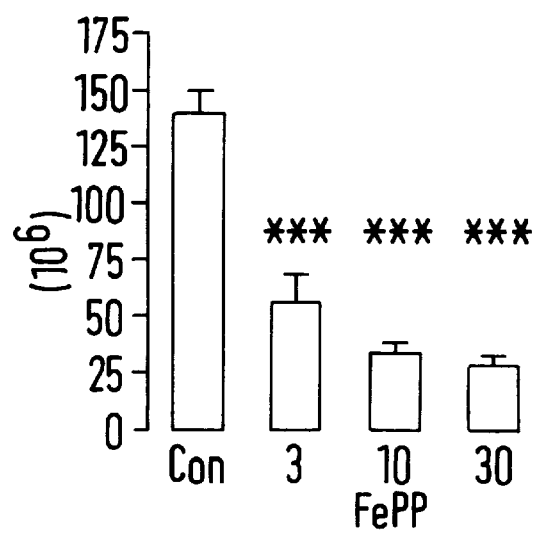

Neither SnPP or FePP treatments had an effect on the inflammatory lesion as compared to vehicle control 6 hours after injection of the carrageenin, the PMNs phase of inflammation, (data not shown). However, 24 hours after injection of carrageenin, when there was a dominance of MNs, animals receiving SnPP (the HO inhibitor) showed a dose dependant increase in inflammatory exudate, with animals dosed 3 μmoles/kg SnPP increasing exudate volume by 70% compared to vehicle control (FIG. 11). It was noted that the highest dose of SnPP (30 μmoles/kg) increased exudate volume further but resulted in a decrease in inflammatory cell number (FIG. 12), the likely explanation the later being a toxic effect. In contrast, animals receiving FePP, the HO inducer, showed a dose dependant suppression of inflammatory cell number and exudate volume (FIG. 13 and FIG. 14), all the dosages used significantly reduced inflammation with the lowest dose of FePP (3 μmole/kg) reducing inflammatory cell number and exudate volume by 90% and 55% respectively compared to vehicle control.

Figure 15:
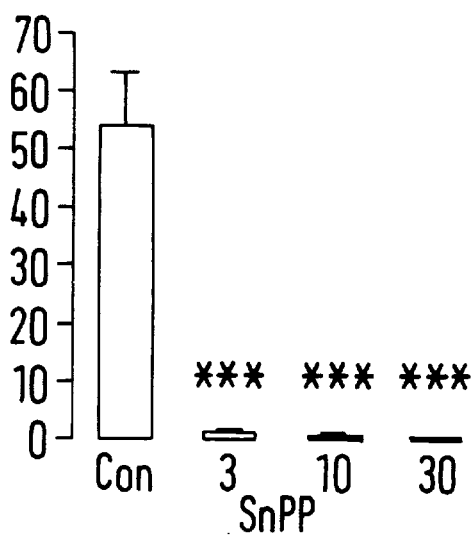
Figure 16:
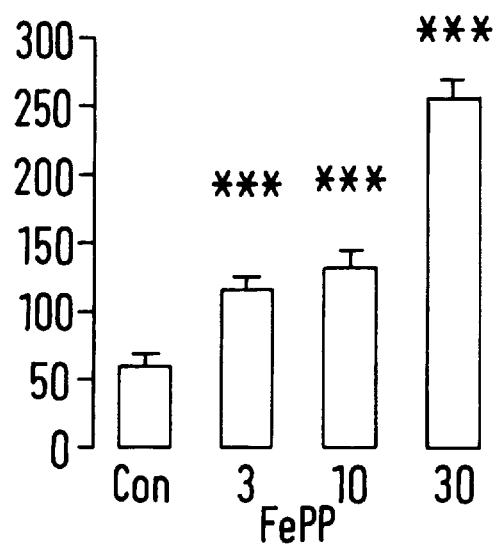

The degree of suppression achieved is greater than that seen with optimal doses of conventional anti-inflammatories or steroids in this model. Analysis of the inflammatory pellets for HO activity confirmed reduction of HO activity with SnPP and increase after treatment with FePP (FIGS. 15 and 16). These finding would support the idea of HO activity being important in the resolution of acute inflammation. The data would also suggest that the main mode of action of SnPP and FePP is via modulation of HO activity and not other mechanisms, as the phenomena appears dose dependant, and the opposing effects of the porphyrins is only observed when HO is expressed.

In conclusion, the findings of this example implicate a direct involvement of HO in the resolution of acute inflammation. The presence of HO in the MNs, a cell type closely associated with chronic inflammation, would support the concept of this enzyme as a modulator of the chronic inflammatory response, and therefore a target for therapies according to the various aspects of the present invention.

EXAMPLE 3

Methods

The brains and spleens of male Wistar rats (160±20 g, Tuck Co. UK) were homogenized using a glass homogenizer, in protease inhibitory buffer; phenylmethylsulfonyl fluoride 1 mM, pepstatin A 1.5 mM and leupeptin 0.2 mM, in 10 mM phosphate buffered saline pH 7.3. Protein determinations were carried by the Bradford method, bovine serum albumin was used as protein standard.

Nitric oxide synthase activity was determined by the citrulline assay and the data calculated as pmol citrulline/mg protein/30 min (Vane, J. R., et al.,*Proc. Natl. Acad. Sci. USA* 91:2046–2050 (1993)).

Heme-oxygenase activity was assayed as previously described (Sierra, E. E. et al., (1992) Analytical Biochem. 200, 27–30).

Briefly, the 15 μl reaction mixture consisted of 11.2 μM [$^{14}$C] heme (specific activity 54 Ci/mol), 1 mM NADPH, 2 mM glucose-6-phosphate, 0.1 units of glucose-6-phosphate dehydrogenase, 3 mg/ml liver cytosolic protein, 100–50 μg of sample protein and the relevant concentration of test drugs; L-arginine, D-arginine, NG-nitro-L-arginine methyl ester (L-NAME) or sodium nitroprusside. The reaction mixture containing the test drugs was allowed to equilibrate at 37° C. for 15 mins before the reaction was started by the addition of the heme. The reaction was terminated after 30 mins by the addition of excess cold heme and bilirubin and placed on ice. The reaction mixture was spotted on to the silica gel thin-layer chromatography sheet by 2, 2 μl applications. All samples were run in duplicate. The chromatogram was developed using a 20:1 dilution of chloroform:acetic acid. Spots corresponding to heme and bilirubin were excised and placed in 10 ml of scintillation fluid to be counted. The data was calculated as pmols bilirubin formed/mg protein/hour.

Statistical analysis of the raw data was carried using Student's unpaired t test. Results expressed as mean ± s.e.mean with P<0.05 considered as significant.

Results

Figure 17:
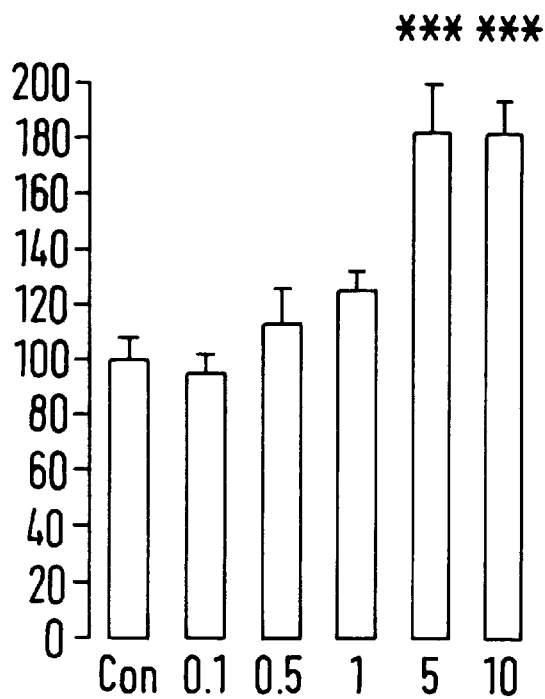
FIGS. 17 and 18 are bar graphs that show the effect of NG-nitro-L-arginine methyl ester (L-NAME) on rat brain and spleen heme-oxygenase activity, FIG. 17—brain homogenates, FIG. 18—spleen homogenates (0.1, 0.5, 1, 5 or 10 mM of L-NAME was incubated with reaction mixture. Results are expressed as percentage activity of control (con) group which received no compound, n=8, *** P<0.001)
Figure 19:
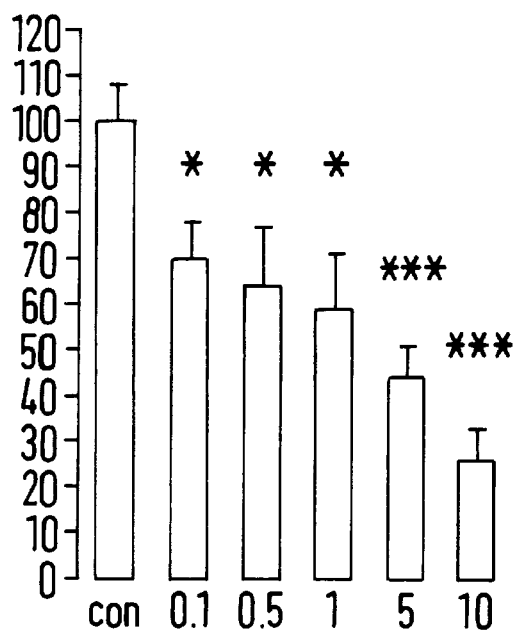
FIGS. 19 and 20 are bar graphs that show the effect of L-arginine on rat brain and spleen heme-oxygenase activity, FIG. 19—brain homogenates, FIG. 20—spleen homogenates. 0.1, 0.5, 1, 5 or 10 mM of L-arginine was incubated with reaction mixture. Results are expressed as percentage activity of control (con) group which received no compound, n=8, * P<0.05, *** P<0.001)
Figure 21:
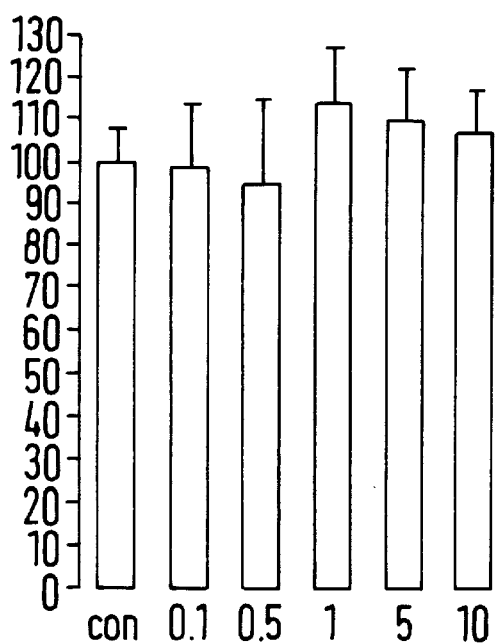
FIGS. 21 and 22 are bar graphs that show the effect of D-arginine on rat brain and spleen heme-oxygenase activity, FIG. 21—brain homogenates, FIG. 22—spleen homogenates. 0.1, 0.5, 1, 5 or 10 mM of D-arginine was incubated with reaction mixture, results are expressed as a percentage of control (con) group which received no compound, n=8)

Homogenates of rat brain contained both HO and NOS activity as determined by our assay systems. In comparison, rat spleen homogenates had double the HO activity, but lacked NOS activity (Table 3). Addition of the NOS inhibitor, L-NAME, resulted in a dose dependent increase in brain HO activity, with 5 mM L-NAME significantly increasing activity by 80% (FIG. 17). Conversely, addition of L-arginine, the NOS substrate, to brain homogenates, resulted in a dose dependent decrease in HO activity (FIG. 19). The highest concentration of L-arginine used, 10 mM, reduced HO activity by 75%. The enantiomer of L-arginine, D-arginine, which cannot be utilized as a substrate by NOS, had no significant effect on brain HO activity (FIG. 21).

Figure 18:
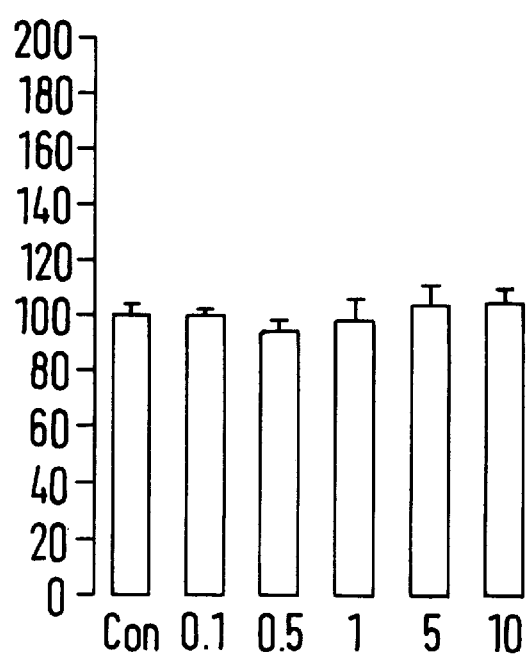
Figure 20:
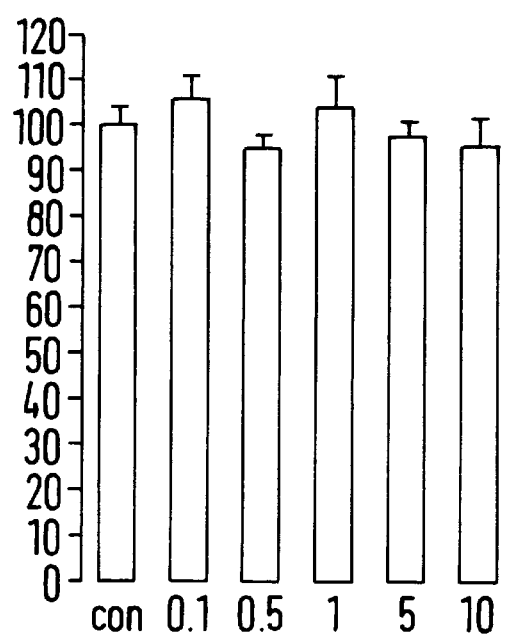
Figure 22:
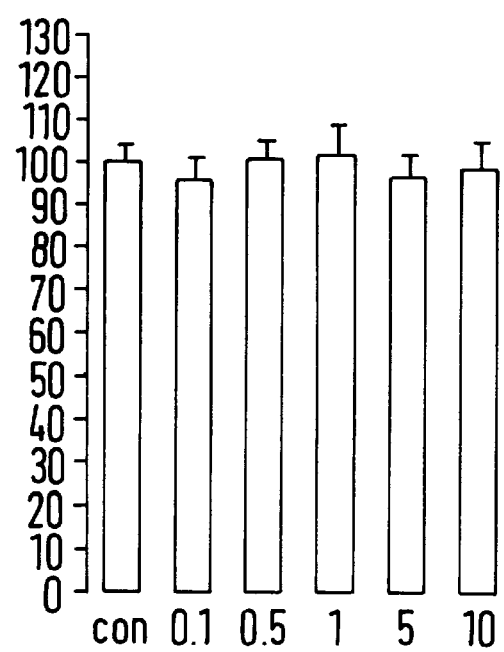

Spleen HO activity, unlike brain activity was not modified by the addition of L-NAME, L-arginine or D-arginine (FIG. 18, 20 and 22 respectively). However the addition of the NO donor sodium nitroprusside resulted in a dose dependent decrease in HO activity in both spleen and brain homogenates (FIGS. 23 and 24). The addition of 10 mM sodium nitroprusside resulted in a 75% and 80% decrease in the HO activity of brain and spleen homogenates respectively.

These results demonstrate that NO, generated by NOS, inhibits HO activity. It is important to note that the isoforms of NOS and HO present in the brain under normal physiological conditions are the constitutive forms of the enzymes, cNOS and HO-2 respectively (Bredt, D. S. et al, (1990) Proc. Natl. Acad. Sci. USA 87, 682–685, and Verma, A., et al., (1993) Science 259, 381–384); whereas spleen under normal physiological conditions contains only the inducible form of HO (Maines, M. D. (1988) FASEB J. 2,2557–2568).

The effects of inhibitors and donors of NO on HO activity have been examined in homogenates of rat brain, where endogenous activity of both NOS and HO are high and in rat spleen where HO is higher, but NOS activity lower than in brain.

We have found that a substrate for nitric oxide, L-arginine (0.1–10 mM), but not D-arginine, decreased heme-oxygenase activity in rat brain homogenates and that the arginine analogue L-NAME (0.1–10 mM) increased activity in the same tissue. In spleen homogenates where endogenous nitric oxide activity is lower than in brain, these compounds had no effect. The nitric oxide donor sodium nitroprusside (0.001 mM–10 mM) reduced heme-oxygenase activity in both brain and spleen.

It is believed by the inventors that in conditions where NOS is induced, the effect of NO modulation of HO activity would be amplified. Further, it is suggested that NO modulates production of the important inflammatory mediators the prostanoids, by its interaction with the heme-containing enzyme cyclo-oxygenase. We have demonstrated an anti-inflammatory role for HO in a model of inflammation. We suggest that NOS and HO have reciprocal modulatory effects in inflammation which effects are the basis for the various aspects of the present invention.

TABLE 1

| Treatment Groups | Exudate Volume (ml) | Total Cells $10^6$ |
|---|---|---|
| 6 hours | | |
| Vehicle injected s.c (n = 27) | 1.26 ± 0.10 | 72 ± 7 |
| SnPP injected s.c (n = 26) | 1.59 ± 0.12 | 67 ± 6 |
| Vehicle injected i.v. (n = 23) | 1.29 ± 0.15 | 69 ± 8 |
| FePP injected iv.v (n = 26) | 0.99 ± 0.11 | 50 ± 8 |
| 24 hours | | |
| Vehicle injected s.c (n = 29) | 0.79 ± 0.12 | 63 ± 6 |
| SnPP injected s.c (n = 24) | 1.80 ± 0.21 | 58 ± 6 |
| Vehicle injected i.v. (n = 22) | 1.37 ± 0.16 | 90 ± 6 |
| FePP injected iv.v (n = 25) | 0.37 ± 0.07 | 45 ± 6 |

TABLE 2

Immunocytochemical analysis of inflammatory cell smears.

| Time | Cell type | % of total cell number* | % +ve for HO-1# | % +ve for HO-2# |
|---|---|---|---|---|
| 2 hours | PMNs | 86 | 0 | 0 |
| | MNs | 14 | 25 | 45 |
| 6 hour | PMNs | >99 | 0 | 0 |
| | MNs | <1 | N.D. | N.D. |
| 12 hours | PMNs | >99 | 0 | 0 |
| | MNs | <1 | N.D. | N.D. |
| 24 hours | PMNs | 62 | 0 | 0 |
| | MNs | 38 | 36 | 41 |
| 48 hours | PMNs | 30 | 0 | 0 |
| | MNs | 70 | 89 | 46 |

*Relative percentage of polymorphonuclear cells (PMNs) and mononuclear cell (MNs) in inflammatory cell smear.
Percentage of PMNs and MNs present, which are positive for heme-oxygenase isoforms. N.D. insufficient cells present for analysis.

TABLE 3

| | brain n = 8 | spleen n = 5 |
|---|---|---|
| Heme-oxygenase activity pmol bilirubin/mg protein/30' | 40 ± 4 | 85 ± 5 |
| nitric oxide synthase activity pmol citrulline/mg protein/30' | 358 ± 78 | 2.38 ± 1 |

Heme-oxygenase and nitric oxide synthase activity in rat brain and spleen homogenates. Mean ± s.e. mean.

Thus, control of inflammation according to the invention is achieved, in embodiments of the invention, by (1) control of HO, or (2) control of levels of nitric oxide, alone or in combination with control of HO.

As many changes can be made to the embodiment of the invention without departing from the scope of the invention, it is intended that all material contained herein be interpreted as illustrative of the invention and not in a limiting sense. All publications, patent applications and patents cited herein are incorporated herein by reference.

What is claimed is:

1. A method of treatment of inflammation associated with a disease selected from the group consisting of rheumatoid arthritis, a chronic inflammatory bowel disease, multiple sclerosis, asthma, airways inflammatory disease, tendonitis, and chronic inflammation in the brain, comprising administering to a mammal in need thereof, other than by topical administration, an effective amount of a compound that alters the activity or amount of heme-oxygenase.

2. A method for treatment of inflammation, comprising administering to a mammal in need thereof an effective amount of a compound that increases heme-oxygenase activity in the mammal.

3. A method according to claim 2, wherein said compound induces the expression of heme-oxygenase.

4. A method of stimulating mononuclear cells in a mammal, comprising administering to a mammal in need thereof, other than by topical administration, an effective amount of a compound that decreases heme-oxygenase activity.

5. A method according to claim 4, wherein said compound is a heme-oxygenase inhibitor.

6. A method according to claim 5, wherein the heme-oxygenase inhibitor is a structural analogue of FePP that inhibits heme-oxygenase.

7. A method according to claim 6, wherein the analogue is selected from SnPP, SnMP, SnDPP, CrPP, CrMP, CrDPP, ZnPP, ZnMP, ZnDPP, MnPP, MnMP, MnDPP, wherein PP equals protoporphyrin, MP equals mesoporphyrin and DPP equals diiododeuteroporphyrin.

8. A method of treating immunosuppression, comprising administering to a mammal in need thereof, other than by topical administration, an effective amount of a compound that decreases heme-oxygenase activity.

9. A method of treatment of chronic inflammation comprising administering to a mammal in need thereof, other than by topical administration, an effective amount of a compound that increases heme-oxygenase activity.

* * * * *